(12) United States Patent
Mikkonen et al.

(10) Patent No.: US 7,824,428 B2
(45) Date of Patent: Nov. 2, 2010

(54) SYSTEM TO BE USED WITH AN IMPLANTING TOOL

(75) Inventors: Joonas Mikkonen, Tampere (FI); Harri Heino, Tampere (FI); Pertti Törmälä, Tampere (FI); Pertti Vesanen, Toijala (FI); Timo Allinniemi, Lempäälä (FI)

(73) Assignee: Bioretec Oy, Tampere (FI)

( * ) Notice: Subject to any disclaimer, the term of this patent is extended or adjusted under 35 U.S.C. 154(b) by 565 days.

(21) Appl. No.: 11/802,692

(22) Filed: May 24, 2007

(65) Prior Publication Data
US 2007/0274800 A1 Nov. 29, 2007

(30) Foreign Application Priority Data
May 24, 2006 (FI) .................................. 20065349

(51) Int. Cl.
*A61B 17/70* (2006.01)
(52) U.S. Cl. ..................... 606/270; 606/300; 606/301
(58) Field of Classification Search ......... 606/264–278, 606/76, 246, 300, 301, 305, 306, 308, 319, 606/325, 328, 232, 104; 411/1, 6, 7, 8
See application file for complete search history.

(56) References Cited

U.S. PATENT DOCUMENTS

| | | |
|---|---|---|
| 2,971,987 A | 2/1961 | Meyers |
| 5,059,210 A | 10/1991 | Clark et al. |
| 5,470,334 A * | 11/1995 | Ross et al. .................. 606/916 |
| 5,868,749 A | 2/1999 | Reed |
| 5,996,453 A | 12/1999 | Blacklock |
| 6,132,435 A | 10/2000 | Young |
| 6,471,707 B1 | 10/2002 | Miller et al. |
| 2002/0099268 A1 | 7/2002 | Paul et al. |

(Continued)

FOREIGN PATENT DOCUMENTS

EP 0276153 A2 7/1988

(Continued)

OTHER PUBLICATIONS

Finnish Search Report (Translation from Finnish Original)—Dec. 15, 2006.

(Continued)

*Primary Examiner*—Eduardo C Robert
*Assistant Examiner*—Summer L Kostelnik
(74) *Attorney, Agent, or Firm*—Venable LLP; Eric J. Franklin

(57) ABSTRACT

The present invention relates a system to be used with an implanting tool having a tip part. The system has a longitudinal axis and comprises a polymeric screw (31) having a head (11) and an adapter between the screw (31) and the implanting tool. The adapter comprises a first part (32) which fits the tip part of the implanting tool. The first part comprises a first element and the system comprises a second element. The first element and the second element are connected to each other with a torque limiting junction having a first maximum torque when the screw is screwed in and a second maximum torque when the screw is screwed off. The shape of the first element and the second element is such that the second maximum torque of the torque limiting junction is greater than the first maximum torque, thus allowing the removal of the polymeric screw (31) from its position.

23 Claims, 9 Drawing Sheets

U.S. PATENT DOCUMENTS

| | | |
|---|---|---|
| 2002/0170115 A1 | 11/2002 | Borders et al. |
| 2003/0054318 A1 | 3/2003 | Gervais et al. |
| 2003/0054319 A1 | 3/2003 | Gervais et al. |
| 2003/0113690 A1 | 6/2003 | Hollander et al. |
| 2005/0145402 A1 | 7/2005 | Hehli et al. |

FOREIGN PATENT DOCUMENTS

| | | |
|---|---|---|
| WO | WO-96/22471 A1 | 7/1996 |
| WO | WO-98/27875 A1 | 7/1998 |
| WO | WO-01/62136 A2 | 8/2001 |

OTHER PUBLICATIONS

European Search Report—Oct. 16, 2007.

* cited by examiner

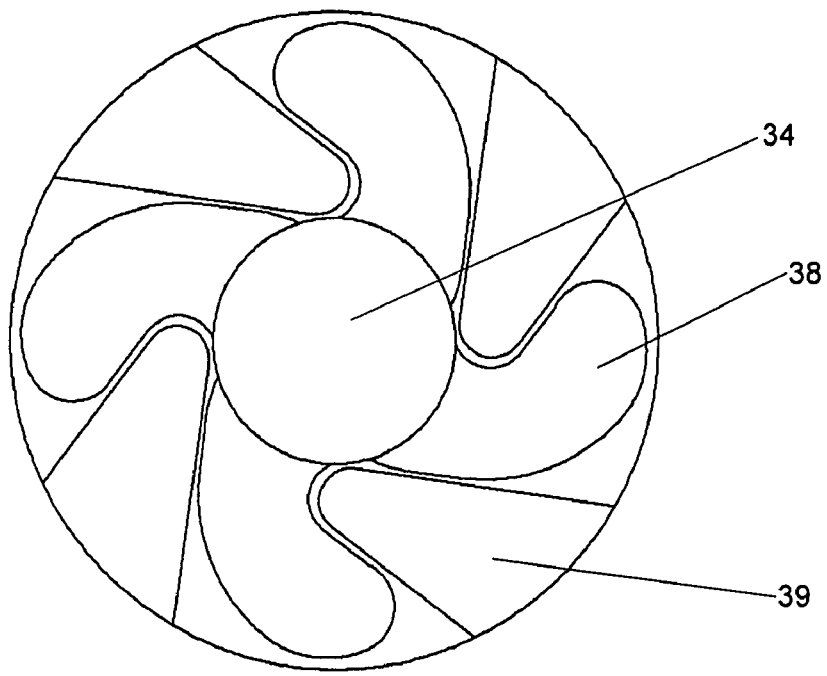
Fig. 11
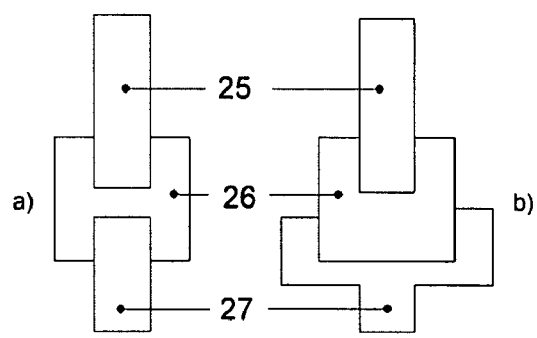
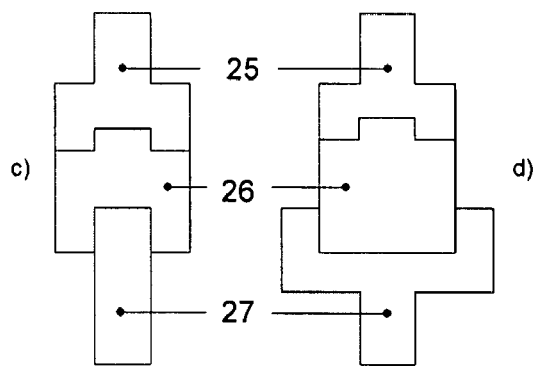
Fig. 12

SYSTEM TO BE USED WITH AN IMPLANTING TOOL

FIELD OF THE INVENTION

The present invention relates to a system to be used with an implanting tool. There is a special adapter between a polymeric screw to be screwed and the implanting tool.

BACKGROUND

Metallic screws have been used for tissue fixation in surgical procedures since he 1940's. Metallic screws preferably made of stainless steel or titanium are still most commonly used in surgery. Metallic materials, however, are significantly stiffer than bone or other tissues in human body. This mechanical incompatibility of the fixation device with the healing tissue generates several problems, such as a stress shielding effect, the loosening of the fixation due to micro motion on the implant tissue interface, and the local necrosis of the tissue due to too high local stresses in the tissue. Additionally, long term complications due to the corrosion products of the fixation devices are not uncommon.

Bioabsorbable fixation devices theoretically overcome all the above mentioned problems related to metallic fixation devices. The modulus of the polymer materials can be tailored to be nearly equivalent with the tissues related to a specific application, which leads to accelerated healing due to biomechanically optimised stress transfer to the healing tissue. Bioabsorption, on the other hand, diminishes the risk of long term complications.

Bioabsorbable fixation devices have not replaced the metallic fixation devices used in surgery as was expected already years ago. There are several reasons for that, such as the lack of confidence on the bioabsorbable products among the clinicians used to perform the operations with metallic devices, and in some cases, the more demanding surgical technique related to the use of the bioabsorbable fixation device. In the case of bioabsorbable fixation screws, the screw head design is strongly limited by the mechanical properties of the bioabsorbable polymer materials. The material properties of bioabsorbable polymers do not allow the usage of standardised bone fixation screw heads, e.g. hexagonal or torx heads.

Most surgical screws have been made of metallic materials, e.g. titanium or stainless steel. These screws have multiple thread and head configurations to be used with different kinds of instrumentation. To ease the work of the orthopedic surgeons, AO/ASIF (Arbeitsgemeinschaft für Osteosynthesefragen/Association for the Study of Internal Fixation) has published proposed configurations of general surgical screws to unify the instruments used in surgery. The surgeons could then use the same instrumentation, drills, taps etc. with implants of different manufacturers, if the implants have been made according to the AO/ASIF proposal. The proposal has also been turned to the ISO standards ISO 5835, ISO 6475 and ISO 9268 and to the ASTM standards ASTM F116-00 and ASTM F543-02.

The AO/ASIF proposal comprises multiple different shapes for the slot of the screw head, such as cruciform, square and hexagonal. The most used one is the hexagonal head. There are also holding sleeves to be attached to the screwdriver, which holds the screw in the driver during the implantation. The AO/ASIF screwdrivers with the holding sleeves have been designed to be used with standard screws.

There are also bioabsorbable screws in use, which are absorbed in the human body after the implantation so that a removal operation is not needed. The problem with AO/ASIF compatible instruments and bioabsorbable screws is that the instruments have been designed to be used with metallic implants. The mechanical properties of the bioabsorbable screws are not adequate to be able to use the AO/ASIF instruments with them. Usually, the bioabsorbable screws have to be implanted with appropriate instrumentation that increases the costs of the operations. Adapters which have been attached to the screw but which only fit the appropriate instruments, have been invented in several cases, see for example U.S. Pat. No. 5,971,987 and EP 0276153. Also, an adapter that fits between the screw and the AO/ASIF instrument has been invented, see U.S. Pat. No. 5,868,749, but the invention has not included the holding sleeve that should also fit the adapter, to be used with it. Moreover, the adapter in question is intended to be used only with screws made of bone substance.

The other problem with the use of bioabsorbable screws is the breaking off of the screw when twisted with the screwdriver. Because surgeons are used to applying metallic screws that can withstand much more torque, the shift to bioabsorbable screws often results in using excessive torque with them. There are torque-limiters invented to be used with both metallic and bioabsorbable screws. Some of them are mechanisms built in the screwdrivers so that the driver gives in when twisted with too much torque (see U.S. Pat. No. 6,132,435). The forces of such torque-limiters have been adjusted to metallic screws and cannot be used with bioabsorbable ones. In many cases, they have also been designed to be used with electrical screwdrivers, which are not appropriate for bioabsorbable screws because it is important to use manual drivers to maintain a better response when tightening bioabsorbable screws. There are also torque-limiters for metallic and bioabsorbable screws that are integrated in the screw (see EP 0276153 and U.S. Pat. No. 6,471,707). They function so that there is a weaker score in the screw head for the purpose that the head will break off when excessive torque is applied. The screw has to be tightened with a secondary instrument, if the screw has not been tightened enough until the head breaks off. Also, if the screw has been stuck, the secondary instrument has to be used to remove the screw.

SUMMARY OF THE INVENTION

According the current invention, the screw can be inserted into the bone with the novel adapter design which enables the use of standard bone screw instruments with holding sleeves and still allows the use of the screw head design best suitable for the polymeric screw. The adapter can comprise one part or several parts. The uppermost part has the standard screw head design and is preferably made of metal. The lowest side of the adapter will fit to a screw head design that is not standardised but optimized for a polymeric bone fixation screw. The lower part may be made of metal and/or plastics. Between the upper and lower parts there is a special junction which limits the maximum torque and which can be transferred from the uppermost part to the lower part in order to avoid breaking of the bioabsorbable polymer screw breakage during the surgical procedure, if a surgeon, who is used to inserting stronger metallic screws, uses too high a torque during the installation. The design of the junction is such that it enables the removing of the screw from the bone even if the torque-limit has been exceeded during the tightening of the screw. The adapter can be attached to the screw head with a mechanical quick coupling so that it holds the screw firmly during the insertion, but after the screw has been tightened enough, the adapter can be easily detached with the screwdriver.

GENERAL DESCRIPTION OF THE INVENTION

The system is to be used with fixation screws, such as bioabsorbable fixation screws. The system is intended to be used with an implanting tool having a tip part. The system comprises an adapter comprising a first part, and a polymeric screw. The adapter may comprise a second part. The system is elongated and has a longitudinal axis. The head of the first part fits the tip part of the implanting tool, e.g. a special screwdriver. The second part of the adapter is compatible with the head of the polymeric screw.

When the adapter comprises the second part, the first and the second parts of the adapter are connected to each other with a torque limiting junction. The torque limiting junction allows the first part to rotate with respect to the second part and the polymeric screw when the predetermined maximum torque has been exceeded during the screwing of the polymeric screw. However, when the polymeric screw is screwed off, i.e. when the tensioning of the polymeric screw is loosened, the first and the second parts do not rotate with respect to each other. Therefore, the polymeric screw can be screwed off although it cannot be tightened any further.

The first part of the adapter comprises a head and a shaft which axis is concentric to the longitudinal axis of the system. The head usually has a larger diameter than the shaft. The head comprises a spot which is compatible with the implanting tool. The spot can be a suitably shaped recess, for example a hexagonal, cruciform, hexalobular, or quadratic recess, or the recess is a single slot. In the end of the shaft there is an end part which forms a connection to the second part.

On the surface of its periphery the shaft comprises a first element which counteracts with a second element in the second part. The first element and the second element together form a body which allows the rotation when the maximum torque is exceeded during the screwing and prevents rotating when the screw is screwed off. The first element may comprise suitably shaped ridges which are provided around the periphery of the shaft. The ridges are shaped so that they can operate in above-described manner in connection with the first element. The number of the ridges or teeth can vary. The ridges can be teeth of a pinion.

The second part is concentric with the longitudinal axis of the system. The second part comprises the second element which forms a counterpart to the first element. The second element may be a cavity whose shape corresponds to that of the first element. In the bottom of the cavity there may be a recess which is compatible with the end portion of the shaft of the first part of the adapter.

The cavity is surrounded by walls which are separated from each other by at least one slot. The slot makes it possible that the walls can bend outwards when the first element has to rotate with respect to the second element. There are usually more than one slot, for example four slots.

On the opposite side of the second part (in the length direction) there is a slot for fastening the polymeric screw. The slot is surrounded by forks which support the head of the screw from their side. The forks may comprise tabs on their inner surface.

The polymeric screw is concentric with the longitudinal axis of the system and it is attached to the second part. The head of the polymeric screw is shaped so that it fits the slot of the second part. The head of the screw may comprise flutes which are compatible with the tabs.

According to another modification, the first element comprises a pinion. The pinion comprises blades which extend towards the periphery of the pinion. The pinion is fastened to an end of a shaft which is compatible with a hole in the second part.

The second element comprises walls whose upper side is beveled in the screwing direction. The walls are placed radially and their height becomes smaller towards the center of the second part. The underside of each blade is stepped so that the walls will grip the steps of the blades when the screw is screwed off.

The materials, the dimensions and the shapes which are used in the adapter are selected so that the desired torque forces can be achieved. The materials are normally selected amongst metals or plastics.

When the adapter does not comprise the second part, the second element is formed on the head of the polymeric screw. The head of the polymeric screw may comprise on its periphery cutting-ins which are compatible with the first element of the first part of the adapter. The first element may comprise fingers which grip the cutting-ins. The cutting-ins and the fingers are shaped so that when the maximum torque in the screwing-in direction is exceeded, it is possible to rotate the screw in the screwing off direction.

As a common feature for all modifications described in this application, there may be a canal for a guide wire. The canal is concentric with the system of the invention and extends through the system to the longitudinal direction of the system.

BRIEF DESCRIPTION OF THE DRAWINGS

FIG. 3 shows a perspective view of a bioabsorbable screw,

FIGS. 6-8 and 10 and 11 show cross-sectional views of a torque limiting junction, FIG. 12 shows schematic views of possible modifications of the system according to the invention.

DETAILED DESCRIPTION

Figure 1:
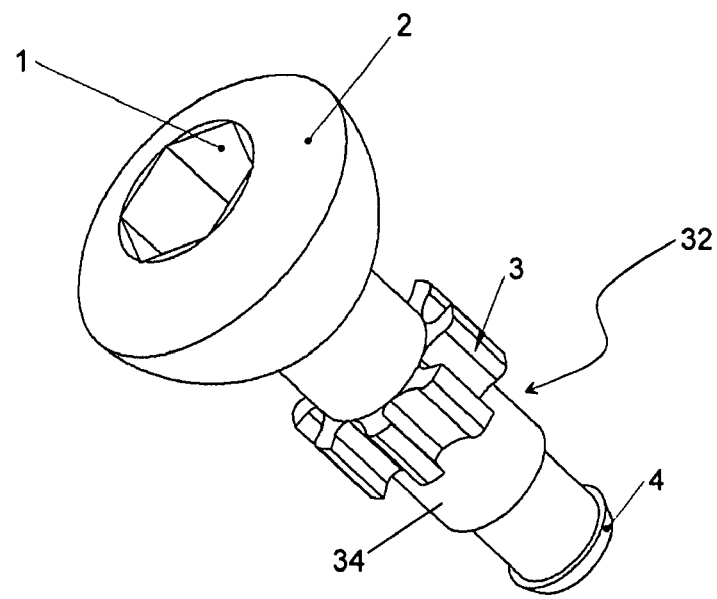
FIG. 1 shows a perspective view of a first part of the adapter.

An example of the first part of the adapter is shown in FIG. 1. The head of the first part comprises a hexagonal slot 1 that fits the AO/ASIF hexagonal screw driver. The first part 32 is also formed in the shape of an AO/ASIF metallic screw head so that it fits the screw holding sleeve 2. In the middle of the first part 32, there are ridges 3 that form part of the torque-limiting element. The sequential ridges 3 are on the periphery of a shaft 34. The ridges 3 are shaped so that they allow torsion in the clockwise direction when the maximum torque in the clockwise direction is exceeded, but grip the counterpart when the first part is turned in counterclockwise direction (in this case, the polymeric screw is screwed to the clockwise direction and screwed off in the counterclockwise direction). In this case, the ridges incline in the counterclockwise direction, i.e. in the screwing-off direction. The end portion 4 of the first part is formed so that it attaches firmly to a recess 8 in the counterpart.

Figure 2:
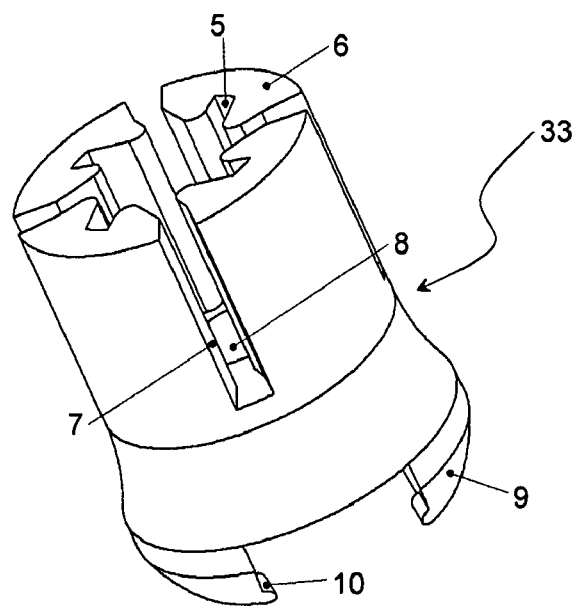
FIG. 2 shows a perspective view of a second part of the adapter.

The counterpart of FIG. 1, i.e. the second part 33, is shown in FIG. 2. There is a cavity 5 of the same form as in FIG. 1 so that the ridges 3 fit inside the part. There are four bending walls 6 that allow the torque-limit to function with the clockwise torsion. The four bending walls are separated with four slots 7. The counterpart, i.e. the first part 32, fits the recess 8 in the middle of the second part 33. The other end of the part has two forks 9 that fit the bioabsorbable screw head. Small tabs 10 allow the part to attach firmly to the screw so that the adapter only comes off with a bending motion.

The polymeric screw 31 is shown if FIG. 3. The head 11 of the screw is formed to fit the adapter by two cuts 12 in both sides of the head. Flutes 13 that fit the tabs of the adapter attach the screw to the adapter. The screw comprises threads 14 and a core 15 underneath the threads below the head 11.

Figure 4:
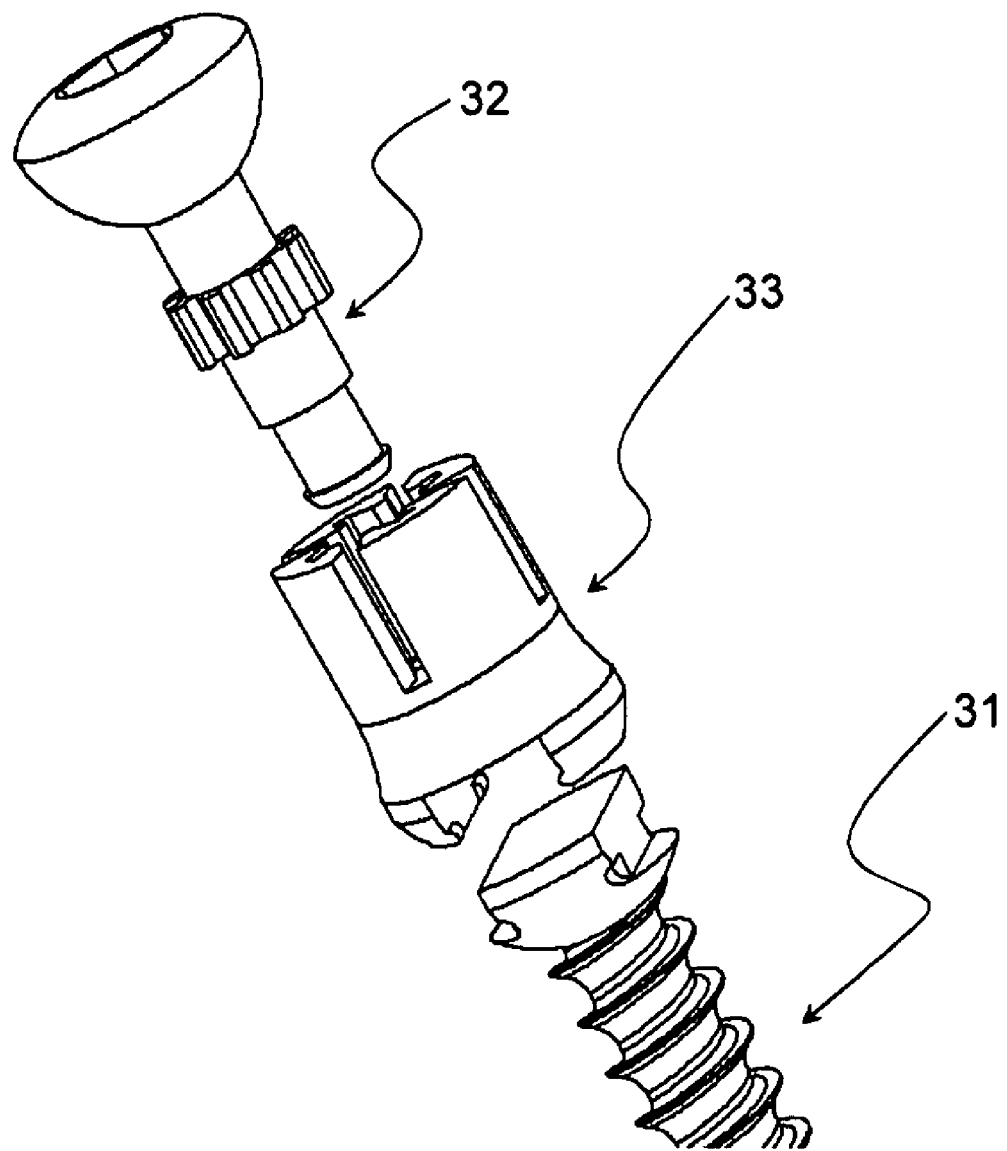
FIG. 4 shows a perspective view of an exploded assembly comprising parts of the system of the invention.
Figure 5:
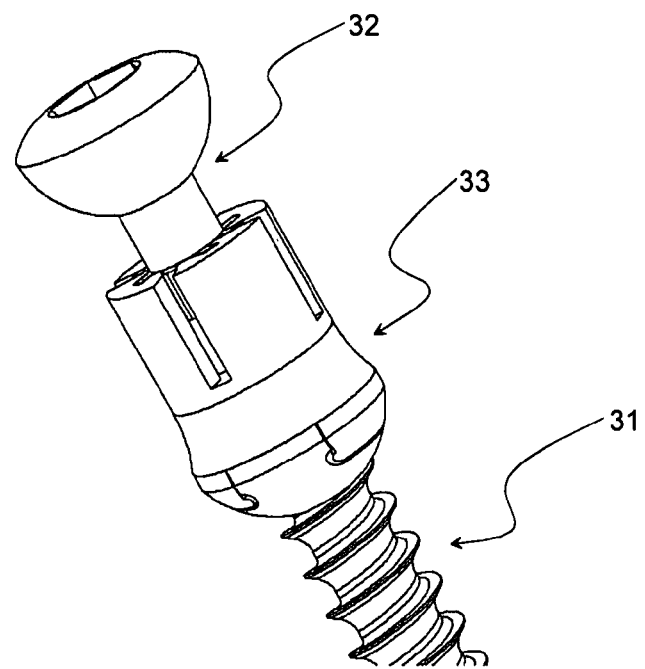
FIG. 5 shows a perspective view of the system of the invention.

There is an exploded assembly of the screw-adapter combination in FIG. 4. The different parts are positioned in their proper places before the assembly. The built up adapter-screw is shown in FIG. 5.

Figure 6:
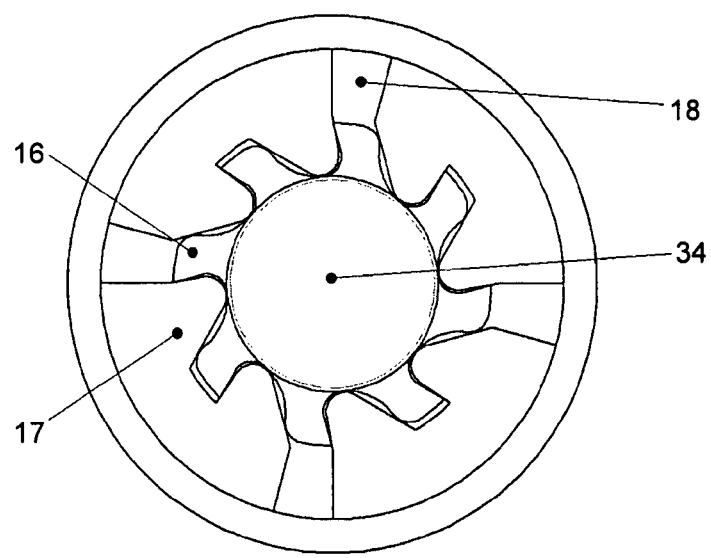

The FIG. 6 shows one modification of the torque-limiting part of the adapter. The shaped pinion 16 allows rotation in the clockwise direction and prevents it in counterclockwise direction (in this case, the polymeric screw is screwed to the clockwise direction and screwed off in the counterclockwise direction). The teeth of the pinion incline in the counterclockwise direction, i.e. in the screwing-off direction. The walls 17 around the pinion 16 restrict the rotation. The slots 18 allow the walls 17 to bend, and with the proper torque, allow the pinion 16 to turn.

Figure 7:
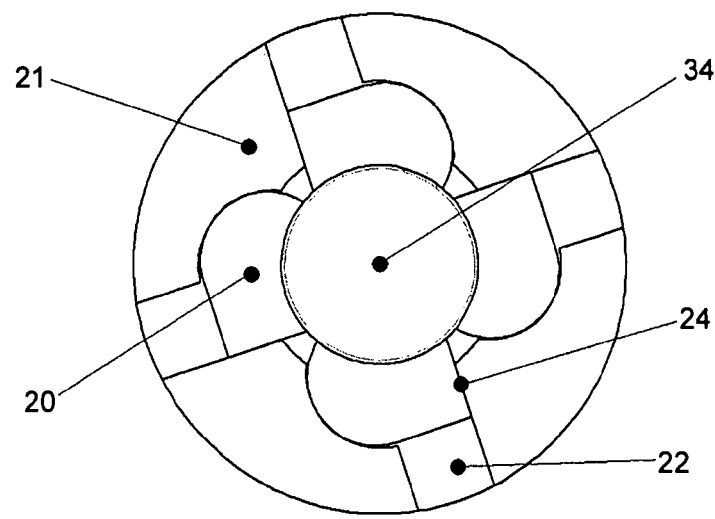

In FIG. 7 there is another modification of the torque-limiting part of the adapter. The shaped pinion 20 is shaped so it can bend walls 21 around it. The slots 22 allow bending of the walls 21 with the proper torque. The counterclockwise rotation is prevented by the blades 24 of the pinion 20 and the walls 21. The blade 24 have a rounded edge and a rectangular edge. The rounded edges of the blades 24 allow the rotation when necessary but the rectangular edges prevents the rotation.

Figure 8:
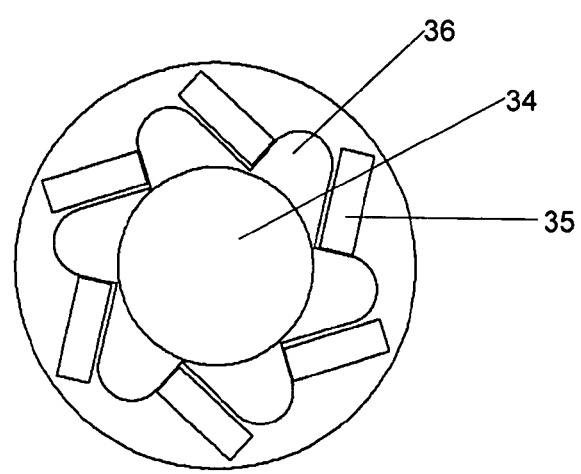
Figure 9:
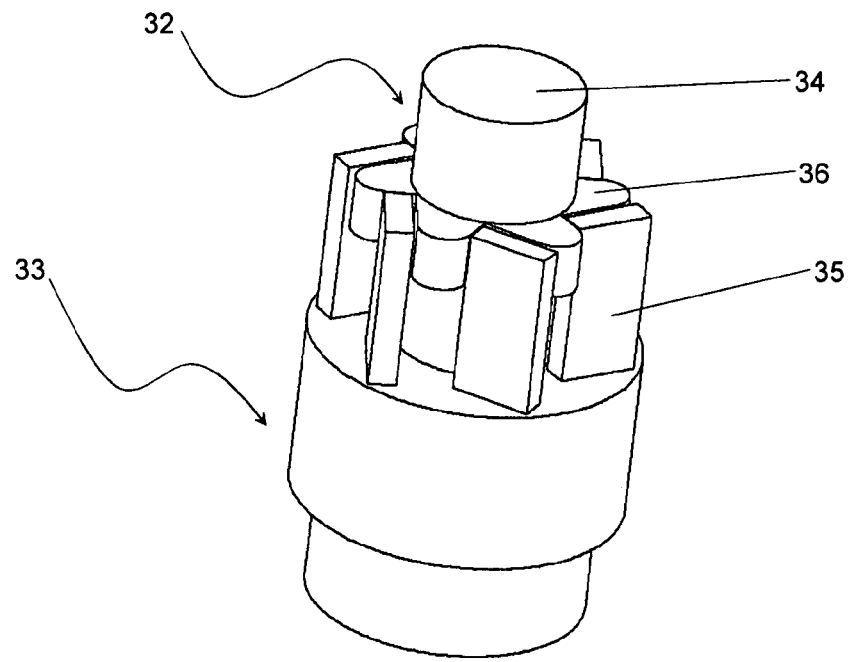
FIG. 9 shows a perspective view of an adapter (a partial view)

FIG. 8 shows still another modification of the torque-limiting part of the adapter. On the shaft 34 of the first part of the adapter there are blades 36 which have rounded edges and incline in the screwing-off direction. The shape of the blades allows the rotation in the clockwise direction and prevents it in the counterclockwise direction (in this case, the polymeric screw is screwed in the clockwise direction and screwed off in the counterclockwise direction). In this case, the blades have rounded edges. Walls 35 keep the blades 36 in their position but when the torsional force is high enough the walls 35 bend and allow the rotation. In the current modification, the walls 35 are individual columns as shown in FIG. 9.

Figure 10:
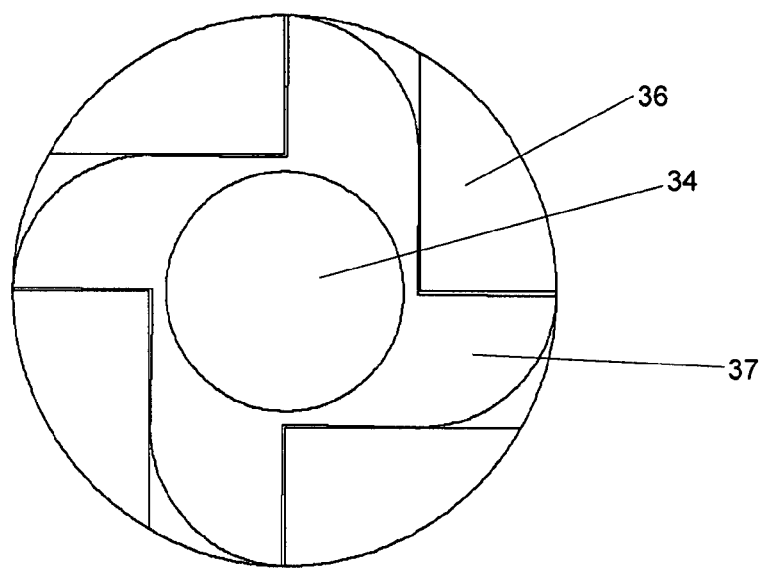

FIG. 10 shows blades 36 which are formed on the shaft 34 and walls 35. The blades comprise a rounded edge and a rectangular edge. The function of the adapter is the same as described also in connection with the other figures.

FIG. 11 shows blades 38 which are formed on the shaft 34 and walls 39. The blades have rounded edges and incline in the screwing-off direction. The function of the adapter is the same as described also in connection with the other figures.

FIG. 12 shows different modifications of the instrument-adapter-screw junctions. The screw 25 can be attached to the adapter 26 with a male or female connection. Simultaneously the instrument 27 can be attached to the adapter 26 with a male or female connection.

Figure 13:
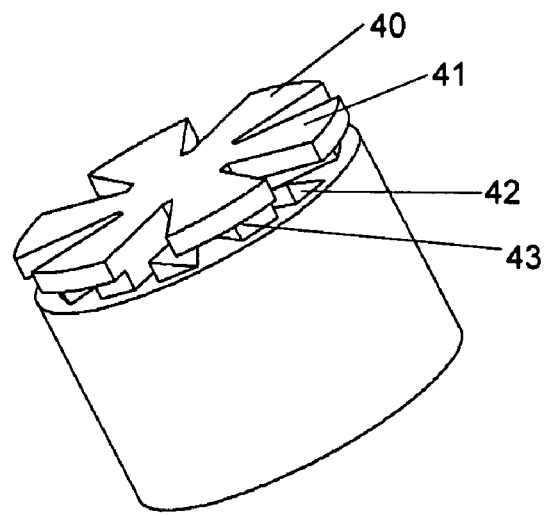
FIG. 13 shows a perspective view of an adapter (a partial view)
Figure 14:
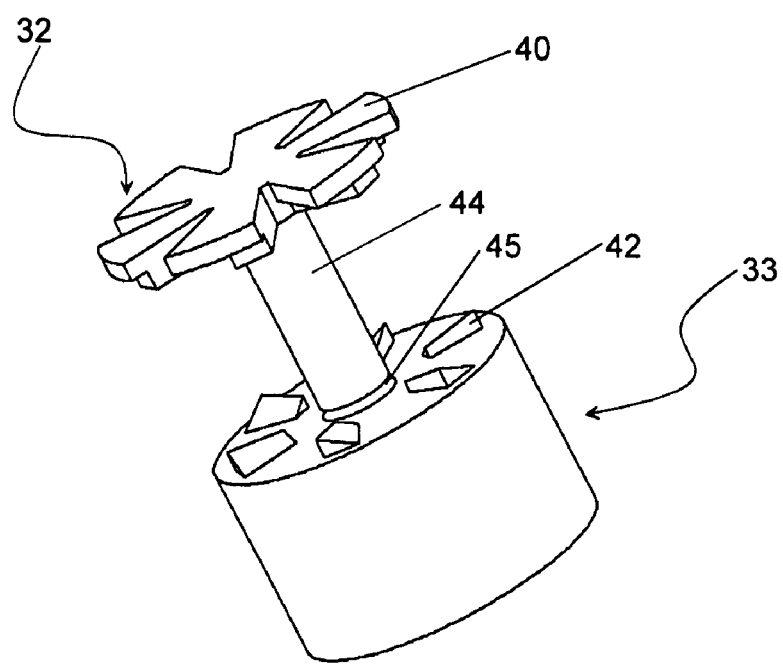
FIG. 14 shows a view of the adapter of FIG. 13 in extended position.

FIGS. 13 and 14 show still another modification of the torque-limiting part of the adapter. The first element comprises a laterally rotating pinion 40. The pinion 40 comprises blades 41 which become larger towards the periphery of the pinion 40.

The second element comprises walls 42 whose upper side is beveled in the screwing direction. The walls 42 are placed radially and their height becomes smaller towards the center of the second part. The underside of each blade is stepped so that the walls will grip the steps 43 of the blades 41 when the screw is screwed off.

The first element also comprises a shaft 44 which is compatible with a hole 45 in the second element. When the shaft 44 is placed in the hole 45 the torque-limiting junction is accomplished.

Figure 15:
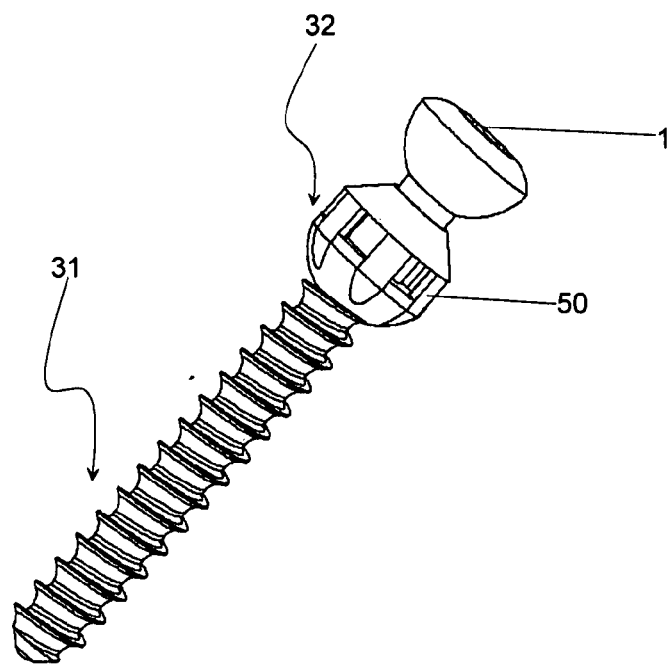
FIG. 15 shows a perspective view of the system of the invention.
Figure 16:
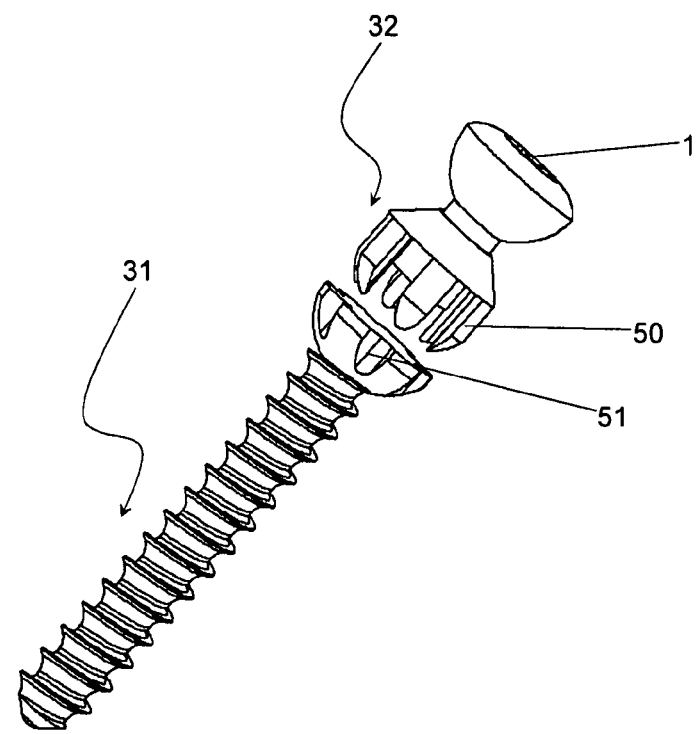
FIG. 16 shows a view of the system of FIG. 15 in extended position.

FIGS. 15 and 16 show a modification of the system of the invention. The system comprises the first part 32 of the adapter but the second part is omitted. The first element of the first part 32 comprises fingers 50. The head of the polymeric screw 11 has cutting-ins 51 which serve as the second element. The fingers 50 and the cutting-ins 51 form counterparts. The fingers 50 bend outwards when the maximum torque in the screwing-in direction is exceeded. However, the screw 31 may still be screwed off if desired.

Figure 17:
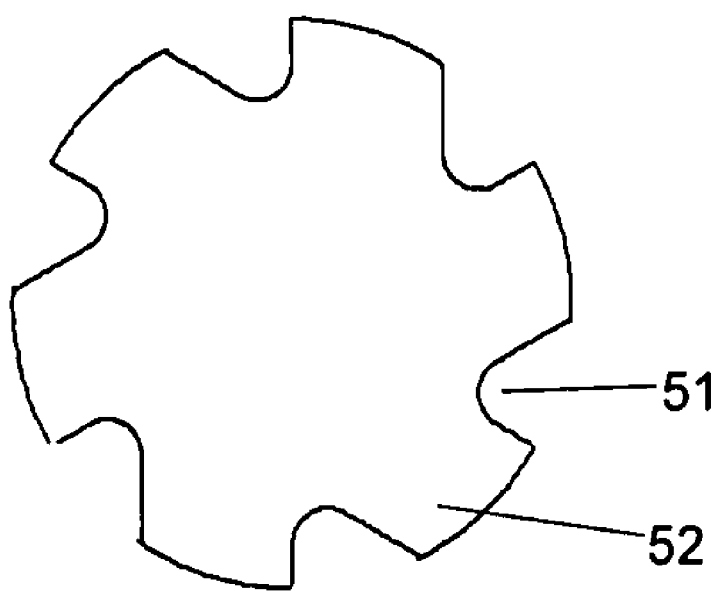
FIG. 17 shows a top view of a head of a polymeric screw.

FIG. 17 shows the head of the polymeric screw 31 shown in FIGS. 15 and 16. The periphery of the head comprises the cutting-ins 51 so that teeth 52 are formed therebetween. The teeth 52 incline in the screwing off direction.

A skilled person can readily construct other modifications in addition to those shown in FIGS. 1-17 after seeing the principle of this invention. Further, it is possible to use both left-handed screws or right-handed screws and a skilled person will understand how to modify the adapter according to the screw to be used.

The invention claimed is:

1. A system to be used with an implanting tool comprising a tip part, the system having a longitudinal axis, the system comprising:
   a polymeric bone fixation screw comprising a head, the polymeric bone fixation screw being concentric with the longitudinal axis of the system,
   an adapter comprising a first part comprising a recess configured to receive the tip part of the implanting tool, the first part being concentric with the longitudinal axis of the system, and the first part comprising a first element, a shaft and ridges on a periphery of the shaft,
   a second element comprising a counterpart to the first element, the counterpart comprising a cavity configured to receive the ridges of the first part, the counterpart further comprising bending walls separated by at least one slot, and
   the first element and the second element are configured to be connected to each other with a torque limiting junction having a first maximum torque in a first torsional direction when the polymeric bone fixation screw is screwed in and a second maximum torque in a second torsional direction when the polymeric bone fixation screw is screwed off, and wherein the second maximum torque of the torque limiting junction is greater than the first maximum torque, thus allowing the removal of the polymeric bone fixation screw from its position.

2. The system according to claim 1, further comprising:
   a second part configured to engage the head of the polymeric bone fixation screw and comprising the second element, the second part being concentric with the longitudinal axis of the system.

3. The system according to claim 2, wherein the at least one slot allows the bending of the walls of the second part.

4. The system according to claim 2, wherein the second part further comprises forks which support the head of the polymeric bone fixation screw.

5. The system according to claim 2, wherein the second part further comprises tabs.

6. The system according to claim 5, wherein the head of the polymeric bone fixation screw comprises flutes which are compatible with the tabs.

7. The system according to claim 1, wherein the head of the polymeric bone fixation screw comprises the second element.

8. The system according to claim 1, wherein the first part is compatible with the implanting tool according to ISO 5835.

9. The system according to claim 1, wherein the recess of the first part is arranged in a head of the first part, and wherein the is hexagonal, cruciform, hexalobular, quadratic, or the recess is a single slot.

10. The system according to claim 1, wherein the adapter comprises at least one of metal or plastic.

11. The system according to claim 1, wherein the polymeric bone fixation screw is bioabsorbable.

12. The system according to claim 1, wherein the polymeric bone fixation screw is attached to the adapter with a quick coupling or a pivot connection.

13. The system according to claim 1, wherein the first part of the adapter is connectable to the polymeric bone fixation screw by either a female connection or a male connection.

14. The system according to claim 1, wherein the ridges are sequentially arranged on the periphery of the shaft.

15. The system according to claim 14, wherein the ridges incline in the screwing-off direction.

16. The system according to claim 14, wherein the ridges comprise teeth of a pinion.

17. The system according to claim 1, wherein the first element further comprises blades comprising a rounded edge and a rectangular edge.

18. The system according to claim 1, wherein the first element further comprises blades comprising rounded edges.

19. The system to claim 1, wherein the first part further comprises an end portion.

20. The system according to claim 19, wherein in a bottom of the cavity of the counterpart comprises a recess which is compatible with the end portion of the first part.

21. The system according to claim 1, wherein the first element further comprises a pinion comprising blades which become larger towards a periphery of the first part.

22. The system according to claim 21, wherein the walls of the second element are arranged radially, have a height that becomes smaller towards a center of the second part, and have an upper side that is bevelled.

23. The system according to claim 1, further comprising:
a canal configured to receive a guide wire, wherein the canal is concentric with the system and extends through the system in a direction of the longitudinal axis of the system.

* * * * *